United States Patent [19]

Flaherty et al.

[11] Patent Number: 5,791,347
[45] Date of Patent: Aug. 11, 1998

[54] MOTION INSENSITIVE PULSE DETECTOR

[75] Inventors: Bryan P. Flaherty, Half Moon Bay; Mark H. Sher; Richard G. Caro, both of San Francisco, all of Calif.

[73] Assignee: Vital Insite, Inc., South San Francisco, Calif.

[21] Appl. No.: 700,647

[22] Filed: Aug. 14, 1996

Related U.S. Application Data

[63] Continuation-in-part of Ser. No. 606,563, Feb. 26, 1996, Ser. No. 556,547, Nov. 22, 1995, and Ser. No. 228,213, Apr. 15, 1994, Pat. No. 5,590,649.

[60] Provisional application No. 06/005,519, Oct. 3, 1995.

[51] Int. Cl.$^6$ ........................................................ A61B 5/00
[52] U.S. Cl. ............................ 128/672; 128/681; 128/687
[58] Field of Search ........................................ 128/667, 668, 128/672, 677–683, 687–690

[56] References Cited

U.S. PATENT DOCUMENTS

| | | | |
|---|---|---|---|
| 3,090,377 | 5/1963 | Salisbury | 128/680 |
| 3,095,872 | 7/1963 | Tulles | 128/680 |
| 4,771,792 | 9/1988 | Seale | 128/774 |
| 4,869,261 | 9/1989 | Penaz | 128/667 |

*Primary Examiner*—Robert L. Nasser
*Attorney, Agent, or Firm*—Flehr Hohbach Test Albritton & Herbert LLP

[57] ABSTRACT

A motion insensitive pulse detector for detecting a patient's pulse includes an exciter adapted to be positioned over a blood vessel of the patient and configured to induce a transmitted exciter waveform into the patient. A noninvasive sensor is adapted to be positioned over the blood vessel and configured to sense a hemoparameter and to generate a noninvasive sensor signal representative of the hemoparameter containing a component of a received exciter waveform. A processor is coupled to the noninvasive sensor and configured to process the noninvasive sensor signal to determine the patient's pulse. Advantages of the invention include the ability to detect a patient's pulse even when the patient is moving or being moved by medical personnel.

30 Claims, 7 Drawing Sheets

MOTION INSENSITIVE PULSE DETECTOR

RELATED APPLICATIONS

This is a continuation in part of the following patent applications and incorporates the applications by reference:

Caro, U.S. Ser. No. 08/606,563 filed Feb. 26, 1996;

Caro, U.S. Ser. No. 08/556,547 filed Nov. 22, 1995;

Caro, Provisional U.S. Ser. No. 60/005,519 filed Oct. 3, 1995; and

Caro, U.S. Ser. No. 08/228,213 filed Apr. 15, 1994, U.S. Pat. No. 5,590,649.

FIELD

The present invention relates to a motion insensitive pulse detector for a patient, and more particularly to a pulse detector that can sense a patient's pulse in the presence of patient motion or other interference.

BACKGROUND

A patient's vital signs are important to monitor when a person is treated by a physician. Among these vital signs is pulse. The pulse is a function of the heart beat which serves to pump blood to all the vital organs of the body. The pulse is commonly sensed by manual palpation of an artery such as the radial artery. Both amplitude and interval of the pulse have clinical significance. Increasingly, it is becoming common for automatic pulse detectors to be used as an alternative to, or adjunct to, manual palpation. There is also developing an increasing awareness that considerable diagnostic information can be obtained by analyzing the detailed shape of the arterial pulse waveform. For all these reasons it is desirable to have a detector that can reliably sense a patient's pulse at a site, such as the radial or carotid artery, and which can provide information to the clinician such as pulse rate, pulse amplitude or pulse shape.

Pulse detection is often performed by medical equipment. This is particularly true in a hospital where a change in pulse can mean that the patient needs immediate medical attention. For example, many surgical facilities have pulse detectors to continuously monitor the patient's pulse during surgery. Moreover, post operative patients are also monitored to insure that their pulse is acceptable for many hours after surgery. In still other cases, pulse detectors are used on patients in private hospital rooms to monitor the patient throughout the night or during other times when they are unattended. Pulse detectors are also used to monitor the patency of arterial grafts after surgery.

While pulse detectors are deployed in various areas of a medical facility, known pulse detectors often fail to properly track the patient's pulse due to motion such as muscle spasms or other muscle movement including respiration, shivering or motion caused by medical personnel. Known pulse detectors can fail to detect a pulse because of patient motion and can erroneously detect patient motion as a pulse. As a result, an alarm might sound or a physician might take action that is not appropriate for the patient at that time. Thus, one limitation of known pulse detectors is their inability to properly detect a patient's pulse in the presence of motion.

A goal of the invention is to overcome the limitations of known pulse detectors and to provide a pulse detector that can properly detect a patient's pulse even in the presence of motion.

SUMMARY

An exemplary embodiment of a motion insensitive pulse detector for determining a patient's pulse includes an exciter adapted to be positioned over a blood vessel of the patient and configured to induce a transmitted exciter waveform into the patient. A noninvasive sensor is adapted to be positioned over the blood vessel and configured to sense a hemoparameter and to generate a noninvasive sensor signal representative of the hemoparameter containing a component of a received exciter waveform. A processor is coupled to the noninvasive sensor and configured to process the noninvasive sensor signal to determine the patient's pulse.

In additional embodiments, the pulse detector includes a filter that separates from the noninvasive sensor signal components that are used to determine the patient's pulse.

Advantages of the invention include the ability to determine a patient's pulse even when the patient is moving or being moved by medical personnel.

BRIEF DESCRIPTION OF THE FIGURES

Additional advantages of the invention will become apparent upon reading the following detailed description and upon reference to the figures, in which.

DETAILED DESCRIPTION

Motion artifact is a significant problem in making accurate physiological measurements related to the cardiac cycle because the frequency range of the cardiac cycle signal overlaps with the frequency range of the motion or other interference. One novel feature of the invention is that it can sense a patient's pulse in the presence of patient motion or other interference. The invention capitalizes on the nonlinear elasticity of the artery to encode relatively low frequency pulse signal information into the propagation velocity of a relatively high frequency excitation signal. Since the pulse signal information is encoded in the high frequency excitation signal, the low frequency motion artifact can be removed by filtering, leaving the high frequency signal unaffected. The low frequency pulse signal information can then be reconstructed from the high frequency excitation signal. This is what is called determining the patient's pulse: constructing the pulse signal from the noninvasive sensor signal by removing interference. It is noted that motion artifact is not the only source of interference to which the invention is insensitive. The invention is insensitive to any source of interference that lies outside the frequency bandwidth of the carrier frequency including electrical interference, vibration, acoustic noise or other electrical or mechanical sources of interference. It is also insensitive to interference that lies within the carrier bandwidth, so long as the interference is not correlated with the carrier. This insensitivity derives from the ability to use correlation techniques such as phase-sensitive detection and lock-in amplification to detect the information encoded on the carrier while rejecting uncorrelated interference.

The invention can be used in a number of different ways. It can be used as a stand-alone pulse monitor that provides a physician with raw information regarding the patient's pulse. It can be used as a stand-alone pulse monitor that provides a physician with processed information regarding the patient's pulse. It can be used to provide another processor with information regarding the patient's pulse and the other processor can use the information to provide a physician with information. For example, another processor could use the pulse information to determine the patient's blood pressure. Additionally, there are a number of alternate uses for the invention that will be evident to one skilled in the art.

Figure 1:
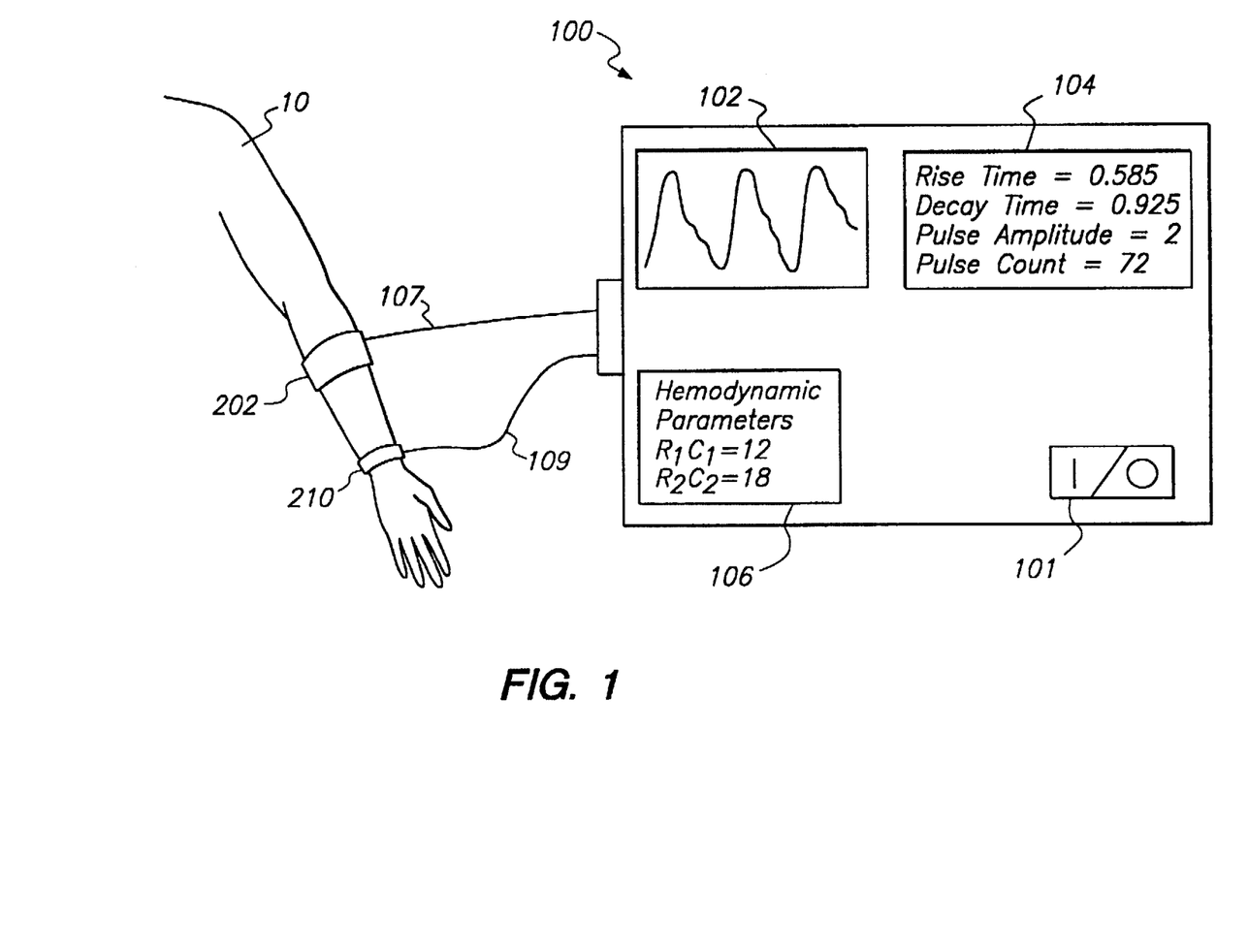
FIG. 1 depicts a motion insensitive pulse detector according to an embodiment of the invention.

FIG. 1 depicts an embodiment of the invention attached to a patient 10. A processor 100 includes a power switch 101, a display 102 for providing a pulse waveform output, a display 104 for providing basic pulse related parameters and a display 106 for providing advanced pulse related parameters. The type of information provided will be a result of the level of detail required for the particular application in which the invention is employed. For example, the pulse waveform is useful in an operating room where the physician desires a visual representation of the pulse. The basic pulse related parameters are also helpful because they provide the physician with easily identified information regarding the pulse rise time, decay time, amplitude and count. The rise time, for example, can be used by a physician to gain insight into the inotropic (muscular contractility) quality of the heart. The advanced pulse related parameters can be helpful in certain situations where the physician desires processed information regarding a primary time constant of the pulse ($R_1C_1$) indicative of the substantial pulse waveform, and a secondary time constant of the pulse ($R_2C_2$) indicative of the ripple in the pulse waveform.

Figure 2:
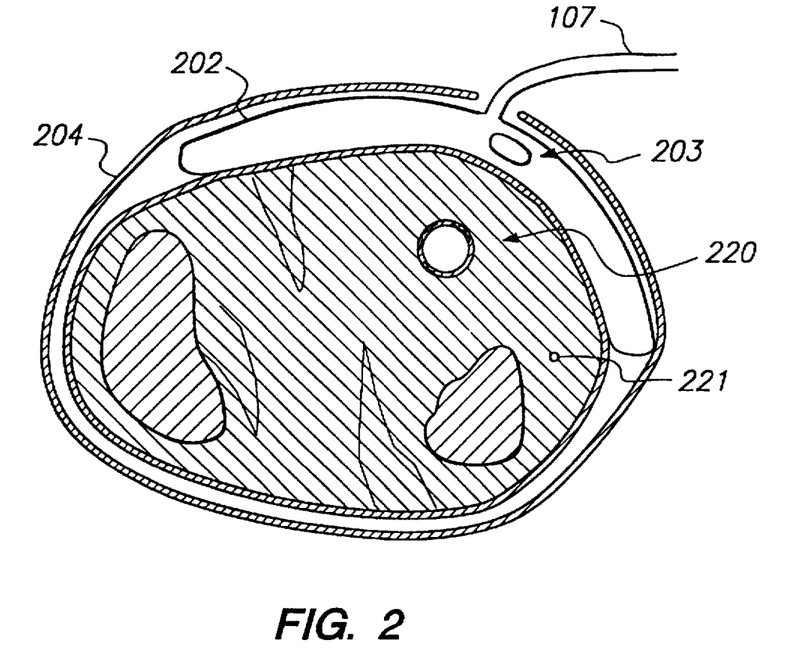
FIG. 2 depicts an exciter attached to a patient.

An exciter 202 is attached to the patient's forearm above the radial artery. The exciter 202 is a device for inducing a perturbation of the patient's body tissue, and is controlled by the processor 100 via tube 107. FIG. 2 shows a cross section of the exciter and its components. The exciter 202 is an inflatable bag attached to the processor via air tube 107. It is fixed in place near an accessible artery 220 by holddown device 204 which can be a buckle, adhesive strap or other device. There can also be an exciter sensor 203 disposed within the exciter to generate a reference signal indicative of the perturbation source waveform, and to deliver the signal to the processor 100. This signal can be used as a reference signal by the processor (explained below). Alternately, the exciter 202 may include a piezoelectric vibrating element coupled to the patient by an interface fluid or gel. There are many other possible embodiments of the exciter as described in U.S. patent application Ser. No. 08/606,563, filed Feb. 26, 1996.

As mentioned above, processor 100 is attached to the exciter via tube 107. The processor 100 controls the pressure in exciter 202 with a transducer and diaphragm. A transducer is a device that transforms an electrical signal to physical movement, and a diaphragm is a flexible material attached to the transducer for amplifying the movement. An example of this combination is a loudspeaker. The diaphragm forms part of an airtight enclosure connected to air tube 107 and an input to initialize the pressure. It will be clear to one skilled in the art that the transducer and air tube 107 and exciter 202 can be miniaturized and combined into a single exciter element capable of acting as a vibrating air filled bag connected to the processor by an electrical drive signal alone or by an electrical drive signal and connection to a source of substantially constant pressure for the bag.

In operation, the pressure is initially established via the initialization input and then the pressure is varied by an electrical signal delivered to the transducer; the diaphragm produces pressure variations in the tube in response to the transducer movement. The result is that the processor, by delivering an oscillating electrical signal to the transducer, causes oscillating exciter pressure. The exciter responds by perturbing the patient's tissue and inducing a transmitted exciter waveform into the patient.

The perturbation excites the tissue 221 and blood vessel 220 below the exciter and causes the transmitted exciter waveform to radiate within the patient's body, at least a portion of which travels along the blood filled vessel. The excitation waveform can be sinusoidal, square, triangular, or of any suitable shape. Experiments conducted to determine a range of satisfactory perturbation frequencies found that the range of 200–1000 Hz works well with a pressure of approximately 1 mm Hg. It is anticipated that frequencies of lesser than 200 Hz and greater than 1000 Hz will also work well, and it is intended that this specification cover all frequencies insofar as the invention is novel.

Figure 3:
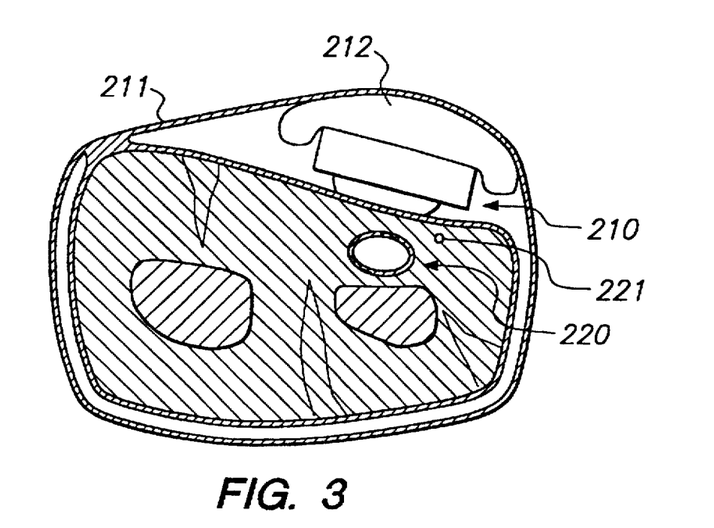
FIG. 3 depicts a noninvasive sensor attached to a patient.

FIG. 1 further shows a noninvasive sensor 210 placed at a distance from the exciter on the patient's wrist. The noninvasive sensor is connected to the processor 100 via wire 109. FIG. 3 shows a cut-away view of the noninvasive sensor 210 placed over the same radial artery 220 as the exciter. The sensor 210 is fixed in place near the artery 220 by holddown device 211 which can be a buckle, adhesive strap or other device. The holddown device 211 also includes a baffle 212 to reduce noise, where the baffle is a pneumatic bag pressurized to hold the sensor 210 at a constant pressure against the patient, for example at a pressure of 10 mm Hg. Alternately, baffle 212 can be any suitable device such as a spring or foam pad.

The noninvasive sensor 210 is responsive to at least one hemoparameter of the patient and generates a signal in response thereto. In this context, a hemoparameter is defined as any physiological parameter related to vessel blood such as pressure, flow, volume, velocity, blood vessel wall motion, blood vessel wall position and other related parameters. In the preferred embodiment a piezoelectric sensor is used to sense arterial wall displacement, which is directly influenced by blood pressure.

As is shown, the sensor is positioned over the radial artery 220 and it is responsive to pressure variations therein; as the pressure increases, the piezoelectric material deforms and generates a signal corresponding to the deformation. The signal is delivered to the processor 100 via wire 109.

The sensor 210 is a transducer that is sensitive to either the pressure of an aplanated artery, the position of the artery wall or the volume of blood in the artery. The sensor is typically a piezoelectric force transducer held down on the artery with sufficient force to detect the pressure oscillations in the artery. The sensor is generally separated from the exciter by some distance (about 5 cm, but a wide range of separations can be used).

Turning to the noninvasive sensor signal, in addition to a natural hemoparameter, the noninvasive sensor signal contains a component indicative of the exciter waveform traveling through the patient. Although the exciter component is designed to be small in comparison to the natural hemoparameter, it contains valuable information. Therefore, the processor 100 is used to separate the received exciter waveform from the natural hemoparameter, and to quantify the respective components to determine the patient's pulse.

Figure 4A:
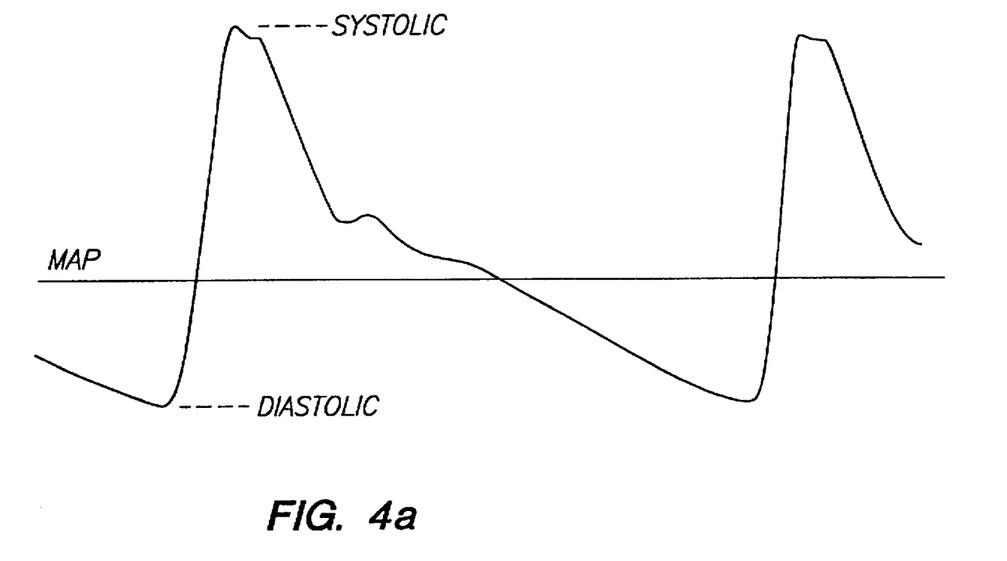
FIG. 4A depicts a pulse waveform.

FIG. 4A shows a natural pulse waveform where the minimum represents the diastolic blood pressure and the maximum represents the systolic blood pressure. Example pressure values are 80 mm Hg diastolic and 120 mm Hg systolic respectively.

Figure 4B:
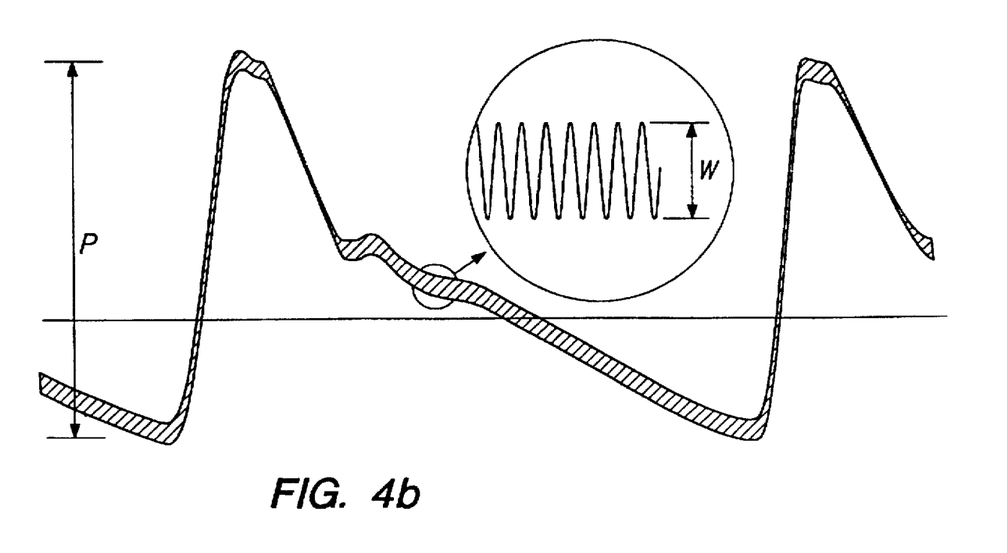
FIG. 4B depicts a pulse waveform with an exciter waveform superimposed thereon.

FIG. 4B shows an operational illustration of the noninvasive sensor signal with an exciter waveform superimposed on a natural pulse waveform. The exciter 202 induces the exciter waveform into the arterial blood at a first location and the exciter waveform becomes superimposed on the natural pulse waveform. Since the exciter waveform is small compared to the patient's natural pulse waveform, the natural pulse waveform dominates as shown in FIG. 4B. As mentioned above, the noninvasive sensor signal contains information regarding both the natural pulse waveform and the received exciter waveform. The processor 100 is designed to process the noninvasive sensor signal to determine the patient's pulse. In one embodiment, the processor separates the constituent components of the noninvasive sensor signal to determine the patient's pulse, as discussed below.

A set of established relationships is used as a basis for the processing performed in the invention. A known relationship exists between blood pressure and exciter waveform velocity. Also, at a given frequency many other relationships are known: a relationship exists between velocity and wavelength, the greater the velocity the longer the wavelength; and a relationship exists between wavelength and phase, a change in wavelength will result in a proportional change in phase. Hence, a relationship exists between blood pressure and phase, and a change in blood pressure will result in a proportional change in phase.

The invention capitalizes on the fact that the propagation velocity of a pressure wave traveling through an elastic tube increases as the stiffness of the tube's wall increases. Arteries can be thought of as elastic tubes whose stiffness increases with the pressure inside the artery. Thus, the velocity of propagation of a pressure wave in an artery will be related to the pressure inside the artery. This has been demonstrated for the natural pulse wave (Geddes, L. A., Hughes, D. J. and Babbs, C. F., Proc. 14th Ann. AAMI Meeting, vol. 14, p. 89 (1969)) and for induced pressure oscillations (Anliker, M., Histand, M. B. and Ogden, E., Circulation Res. vol. 23, p. 539, (1968)).

The propagation velocity can be measured by inducing a high frequency oscillation in the artery with an exciter and detecting the high frequency oscillation at some known distance from the exciter. The velocity is calculated by dividing the distance between the exciter and detector by the time it takes for the oscillation to propagate from the exciter to the detector. This velocity can be continuously calculated and will track the blood pressure. If the frequency of oscillation is higher than the frequency content of arm motion, the high frequency part of the signal will not be affected by the motion and the calculated velocity will continue to track blood pressure even if the low frequency signal contains significant motion artifact.

Note that it is not necessary to calculate velocity to monitor the pulse. The time delay between the exciter and detector is related to blood pressure as is the phase of a sinusoidal pressure oscillation. Therefore, the pulse can be monitored by tracking the phase of the exciter waveform.

Figure 5:
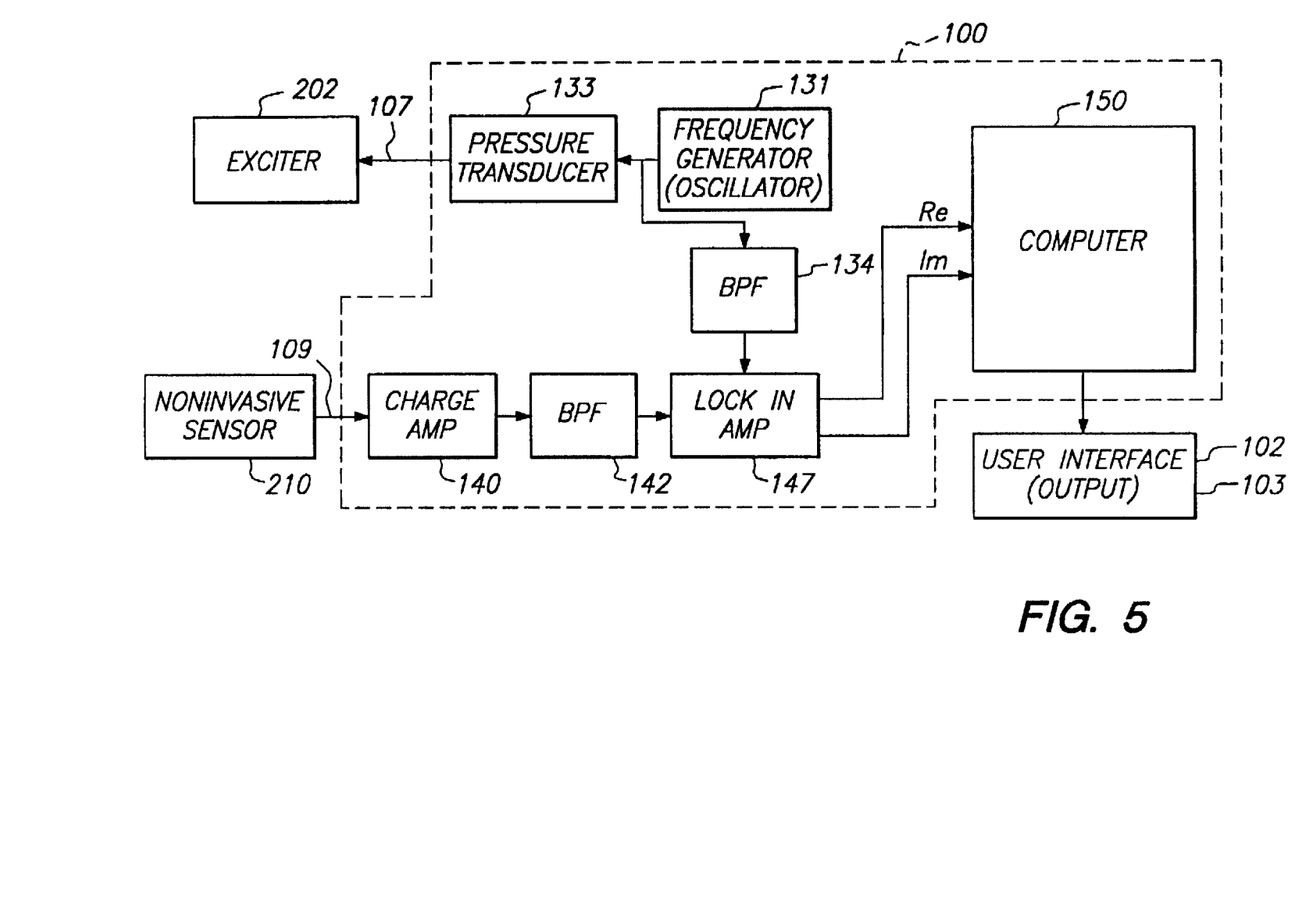
FIG. 5 depicts a schematic diagram according to an embodiment of the invention.

FIG. 5 depicts a schematic diagram of the preferred embodiment. There is an induced wave frequency generator 131 coupled to a pressure transducer 133 that transforms an electrical input to a pressure output. The transducer output is connected to the exciter 202 and controls the exciter's oscillations for inducing the exciter waveform into the patient's arterial blood.

Figure 6:
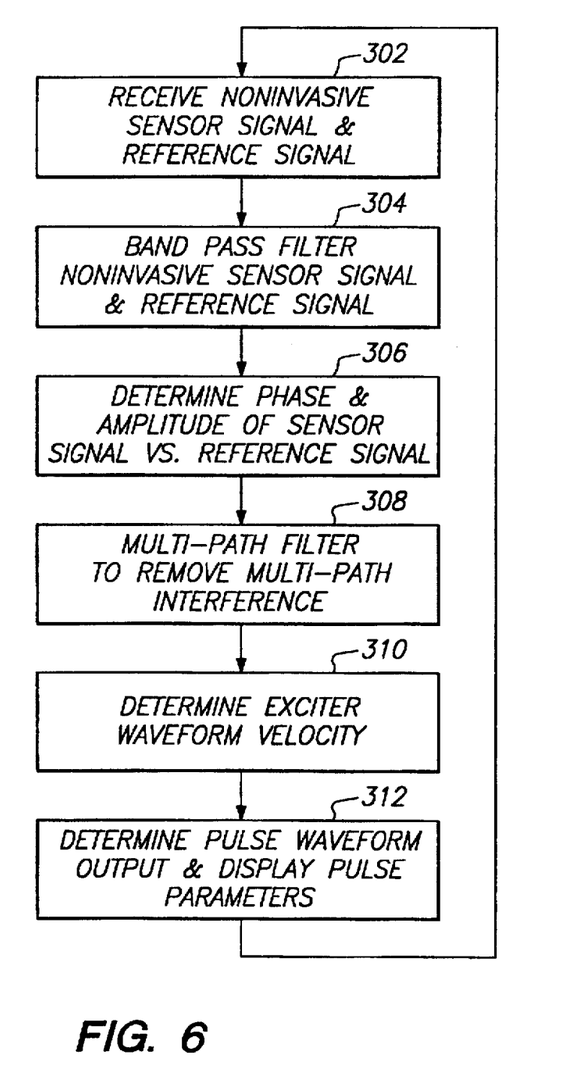
FIG. 6 depicts a processing flow chart according to an embodiment of the invention.

Operation of the invention is described with reference to the FIG. 6 flowchart and the FIG. 5 schematic. The operation begins at step 302 with the receipt of the reference signal from frequency generator 131 and the noninvasive sensor signal from sensor 210. The noninvasive sensor signal is fed to a charge amplifier 140 to amplify the signal from the piezoelectric sensor. The reference signal is fed to band pass filter 134 and the noninvasive sensor signal is fed to band pass filter 142.

In step 304, the reference signal is filtered by band pass filter 134 and the noninvasive sensor signal is filtered by band pass filter 142. The band pass filter 142 removes frequencies outside the frequency band of interest, for example, 200–1000 Hz. At this point, both the natural pulse waveform and any motion induced signals in the frequency range below the band pass filter have been removed from the noninvasive sensor signal. The filtered signals are sampled at a rate of 3200 samples per second with a 14 bit resolution and delivered to the lock-in amplifier 143 signal input. It is anticipated that the sampling rate and resolution can be varied with good results.

In step 306, the lock-in amplifier 143 receives inputs from band pass filter 134 as a reference signal (transmitted exciter waveform) and band pass filter 142 as a noninvasive sensor signal (received exciter waveform). The lock-in amplifier 143 and computer 150 perform a technique known as phase-sensitive detection to single out a component of the noninvasive sensor signal at a specific reference frequency and phase corresponding to that of the reference signal. Phase-sensitive detection provides the resulting received exciter signal with great accuracy and immunity from interference. At this point, any "noise" that is not directly correlated with the exciter signal will have been removed from the received exciter signal.

The lock-in amplifier 143 produces an internal, constant-amplitude sine wave that is the same frequency as the reference signal and locked in phase with the reference signal. This sine wave is then multiplied by the noninvasive sensor signal and low-pass filtered to yield a signal proportional to the amplitude of the noninvasive sensor signal multiplied by the cosine of the phase difference between the noninvasive sensor signal and the reference. This is known as the in-phase or real output.

The lock-in amplifier 143 also produces an internal reference sine wave that is 90 degrees out-of-phase with the reference input. This sine wave is multiplied by the noninvasive sensor signal and low-pass filtered to yield a signal proportional to the amplitude of the noninvasive sensor signal multiplied by the sine of the phase difference between the noninvasive sensor signal and the reference. This is known as quadrature or imaginary output.

The lock-in amplifier 143 then provides the computer 150 with information regarding the in-phase and quadrature components of the received exciter signal as referenced to the phase of the transmitted exciter signal. Alternately, the amplifier can provide components representing the magnitude and phase of the noninvasive sensor signal. In the preferred embodiment, the lock-in amplifier output is sampled at a rate of 200 samples per second with a 14 bit resolution. It is anticipated that the sampling rate and resolution can be varied with good results.

While the phase-sensitive detection performed by the lock-in amplifier is advantageous for identifying in-phase and quadrature components of the noninvasive sensor signal, some multi-path interference remains. The multi-path interference is a result of a signal derived from the exciter that travels to the noninvasive sensor by an alternate path, other than that along the artery taken by the signal of interest. Examples include bones conducting the exciter waveform and the surface tissue such as the skin conducting the exciter waveform.

In step 308, computer 150 performs a multi-path rejection filter procedure on the received exciter waveform. The multi-path rejection filter calculates the effect of the non-arterial paths and subtracts this effect from the measured signal. The resulting signal is the phase and amplitude of the propagated oscillation referenced to the oscillator signal. The multi-path rejection filter was first described in U.S. patent application Ser. No. 08/228,213, filed Apr. 15, 1994, and is described here for the present application.

Figure 7A:
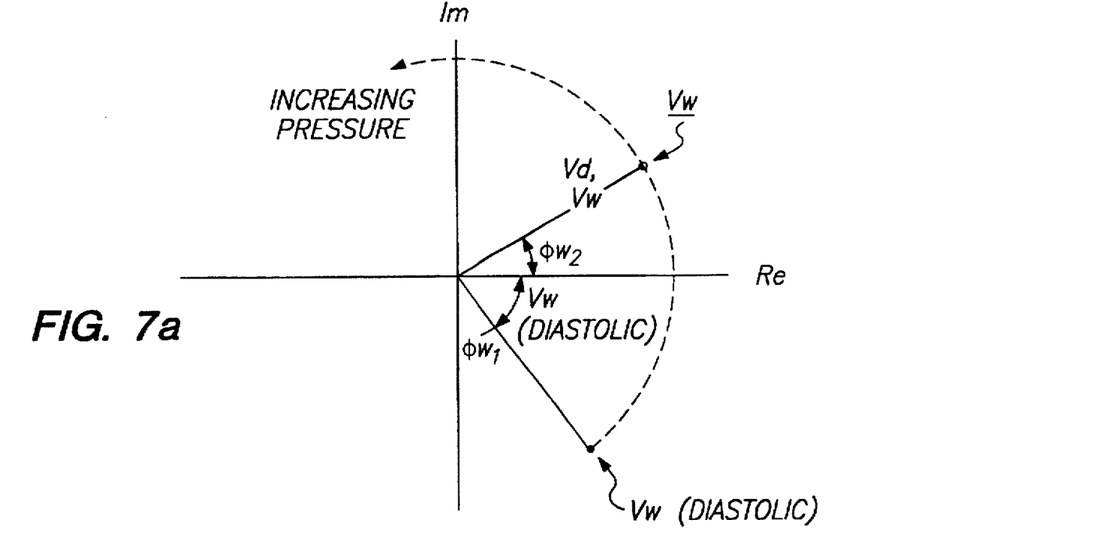
FIGS. 7A–C are graphical illustrations of filter procedure according to an embodiment of the invention.
Figure 7B:
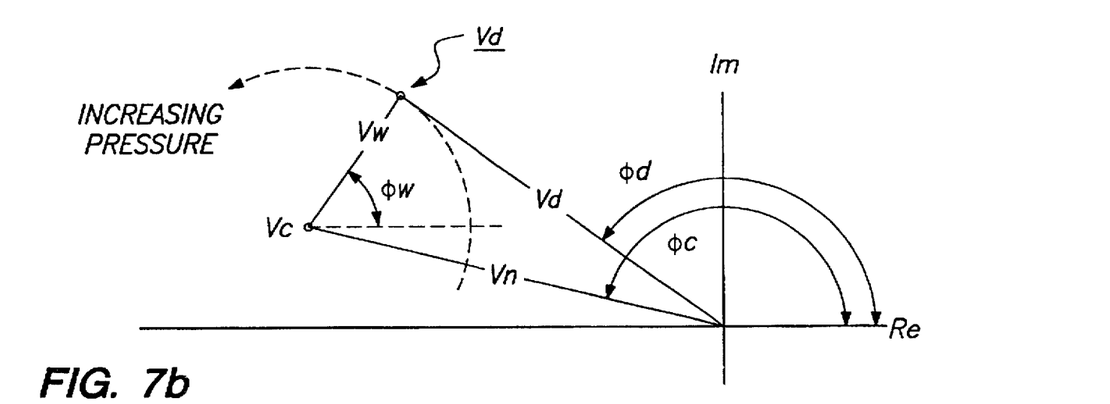
Figure 7C:
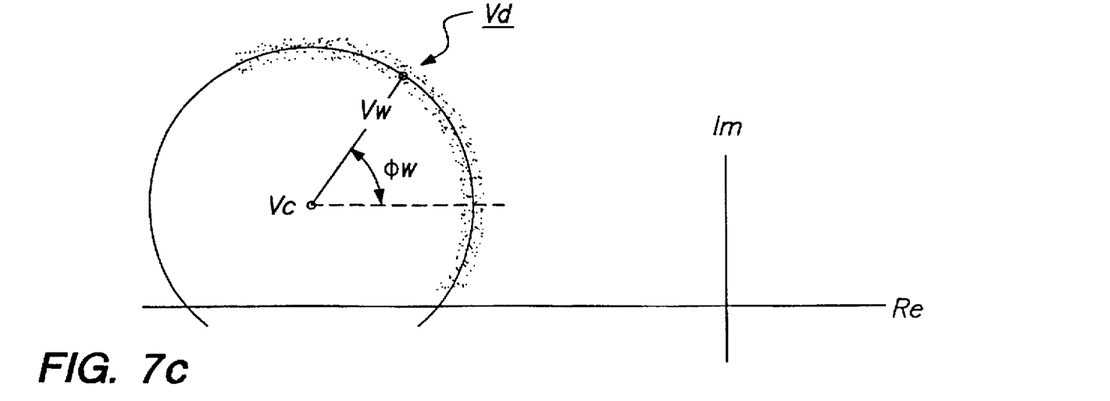

FIGS. 7A–C illustrate the procedure for filtering the received exciter waveform. During a natural pulse, the received exciter waveform represented as vector $V_d(t)$ defines a collection of points that are generated in the complex plane by the real and imaginary outputs of the lock-in amplifier 143. FIG. 7A illustrates the received exciter waveform $V_d(t)$ in the absence of noise. In the absence of noise, $V_d(t)$ is the same as a signal exciter waveform represented as vector $V_w(t)$ which has a magnitude and phase corresponding to the received exciter signal without noise or interference. During a pulse, the magnitude of $V_w(t)$ remains substantially constant, but the vector angle $\Phi_w$ periodically oscillates between a first angle $\Phi_{w1}$ representing a slower velocity (lesser arterial pressure) to a second angle $\Phi_{w2}$ representing a faster velocity (greater arterial pressure). Note that in the absence of noise, the collection of points represented as $V_d(t)$ forms an arc with a center at the origin.

FIG. 7B represents the noninvasive sensor signal $V_d(t)$ in the presence of noise, which is indicated by vector $V_n(t)$. Vector $V_d(t)$ has a magnitude and phase according to the signal exciter waveform $V_w(t)$ plus noise $V_n(t)$. As can be seen in FIGS. 7B–C, vector $V_d(t)$ defines a collection of points forming an arc having a common point $V_c$ substantially equidistant from each of the points in the collection. The vector $V_w(t)$, from $V_c$ to the arc, corresponds to the true magnitude and phase of the signal exciter waveform. The vector $V_n(t)$ represents noise and, once identified, is removed from the received exciter waveform. The remaining component is the signal exciter waveform $V_w(t)$. In practice, an important feature of the signal exciter waveform $V_w(t)$ is the angle $\Phi_w(t)$ that is made between the signal exciter vector $V_w(t)$ and a horizontal line parallel to real axis because the angle $\Phi_w(t)$ is closely related to the pulse waveform. The filter step removes the noise component $V_n(t)$ and retains the signal exciter waveform $V_w(t)$ and angle $\Phi_w(t)$.

The multi-path filter serves to remove noise component $V_n(t)$ (multi-path interference) from the received exciter waveform $V_d(t)$ to provide the signal exciter waveform $V_w(t)$ and angle $\Phi_w(t)$. In addition, the multi-path rejection filter makes the invention insensitive to noise in the frequency bandwidth of the carrier, as long as the noise has an amplitude and phase that changes slowly compared with the timescale of a cardiac cycle.

In the discussion above, it was assumed for illustrative purposes that the magnitude of $V_w(t)$ remains constant over the time of a pulse. In some cases the attenuation of the exciter waveform as it propagates along the artery is pressure dependent, and in those cases the magnitude of $V_w(t)$ can vary during the pulse in a way that is correlated to pressure. Under such circumstances the shape of the figure traced out in the complex plane by the vector $V_d(t)$ will deviate from a perfect circle segment. A typical shape is that of a spiral with a form that can be predicted theoretically. The function of the multi-path filter under such circumstances is conceptually similar to that described above, except that the elimination of the noise vector $V_n(t)$ involves locating $V_c$ at the origin of a spiral segment arc rather than of the center of a circle segment arc. In either case, the term arc is meant to encompass any angular movement of the vector $V_w(t)$ including circle segments and spiral segments.

In step 310, the computer 150 determines the exciter waveform velocity from the signal exciter waveform $V_w(t)$ and angle $\Phi_w(t)$, where the angle $\Phi_w(t)$ represents the phase relationship between the signal exciter waveform and the reference signal. Since a change in the velocity of the exciter waveform causes a corresponding change in phase, and since the phase relationship is known from steps 306 and 308, the velocity of the exciter waveform can be determined from the known change in phase over time $\Phi_w(t)$. Further, since the velocity of the exciter waveform is representative of the pulse, the velocity over time is provided to display 102 as the pulse waveform.

Computer 150 can determine basic pulse parameters of the pulse waveform by identifying specific segments of the pulse waveform and calculating the parameters. For example, the computer can identify the low value and the peak value and calculate the rise time as the time between the low value and the peak value. The computer can calculate the decay time ad the time between the peak value and the low value. The computer can track the magnitude of the signal exciter waveform $V_w(t)$ and display the RMS value to provide the physician with information, for example, about the pulse strength. The computer can also track the pulse count by counting the number of times the pulse crosses a predetermined threshold. These basic pulse parameters serve to provide the physician with easily identified characteristics of the pulse.

Computer 150 can determine advanced pulse parameters of the pulse waveform by calculating the hemodynamic parameters of $R_1 C_1$ and $R_2 C_2$. The $R_1 C_1$ parameter is indicative of the inotropic (muscle contractility) character of the heart and is calculated as the time constant of the large deviations of the pulse waveform. The $R_2 C_2$ parameter is indicative of the impedance match between the heart and the circulatory system. These advanced pulse parameters serve to provide the physician with characteristics of the heart and circulatory system.

In step 312, the pulse waveform is displayed on display 102. Additionally, basic pulse information can be displayed on a display 104 and advanced pulse information can be displayed on a display 106. The information displayed is a function of the application of the invention and whether the physician requires the information.

In another embodiment, the multi-path rejection filter is not required. If a basic motion insensitive pulse detector is desired, the basic model can be constructed without the multi-path rejection filter and still provide many of the advantages of the invention.

In another embodiment, the computer 150 is not required. The lock-in amplifier 143 can perform the functions of calculating the time delay between the exciter and detector, the velocity, the group velocity or other measurements relevant to the application.

In yet another embodiment, the detector 210 and exciter 202 are placed over substantially the same location on the patient's artery. The exciter provides a constant amplitude pressure perturbation to the artery, which causes an arterial wall motion perturbation. The amplitude of the wall motion perturbation is sensed by the sensor. Since wall motion for a given perturbation is dependent on arterial compliance, the variation of arterial compliance during a cardiac cycle results in a variation of arterial wall motion amplitude. Thus, the arterial wall motion sensed by the sensor at the frequency of the exciter's perturbation varies with the arterial pulse.

CONSTANT DISPLACEMENT/PRESSURE EMBODIMENT

Figure 8A:
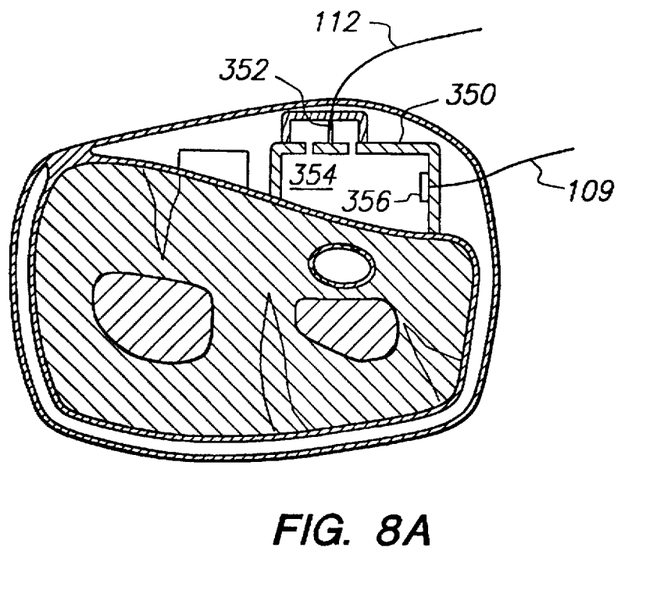
FIGS. 8A–B depict a noninvasive sensor attached to the patient according to another embodiment of the invention.
Figure 8B:
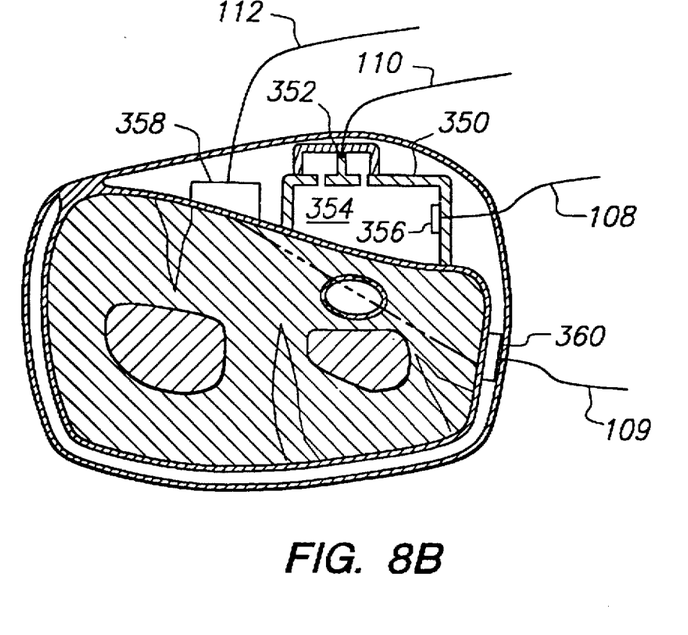

FIGS. 8A–B depict a noninvasive sensor attached to the patient according to another embodiment of the invention. With reference to this embodiment, two aspects of the invention are described: a first involves constant displacement, and a second involves constant pressure.

An exciter assembly 350 includes a vibrating element 352, such as a piezoelectric transducer, to induce the transmitted exciter waveform into the patient. Element 352 is coupled to the processor 100 via cable 110. The exciter assembly 350 provides a chamber 354 above where the exciter is positioned over the patient. This chamber 354 is filled with a fluid, such as water, in order to couple the vibrating element 352 to the patient. Also enclosed in the chamber is an exciter sensor 356 that provides a pressure signal to the processor 100 via cable 108. The pressure signal from the exciter sensor 356 can be used in two ways. In the first aspect of the embodiment the exciter sensor signal is used to provide the noninvasive sensor signal to the processor 100 to determine the patient's pulse. In the second aspect of the embodiment the exciter sensor signal is used to insure that the vibrating element 352 provides a constant pressure to chamber 354.

A. Constant Displacement

In a constant displacement aspect of the embodiment shown in FIG. 8A, vibrating element 352 provides a constant displacement to chamber 354. In this aspect, the pressure perturbation is dependent on the patient's arterial compliance. Since the vibrating element 352 provides a constant displacement to the chamber 354, the resulting sensor signal amplitude (from sensor 356) is proportional to the compliance of the patient's artery. If the artery is highly compliant (flexible), the noninvasive sensor signal will have a relatively small amplitude as the pulse propagates through the artery. If the artery is not compliant (stiff), the noninvasive sensor signal will have a relatively large amplitude as the pulse propagates through the artery. As a result, the noninvasive sensor signal amplitude provides information that is directly dependent on the patient's arterial compliance. This information is very useful to physicians. Since compliance varies as pressure varies during the pulse, the noninvasive sensor signal amplitude varies as the pressure varies during the cardiac cycle. Thus, this embodiment also provides a convenient, motion insensitive, method for determining the pulse.

B. Constant Pressure

In a constant pressure aspect of the embodiment shown in FIG. 8B, vibrating element 352 provides a constant pressure to chamber 354. Exciter sensor 356 provides a feedback exciter sensor signal to the processor 100 to insure a constant pressure of vibrating element 352.

A noninvasive sensor assembly is added to this aspect of the invention. The noninvasive assembly is, for example, a photoplethysmograph. In this example a light source 358 is positioned on a first side of the patient's artery and a light detector 360 is positioned on an opposite side of the patient's artery. The light source 358 provides a constant light power and the detector 360 provides a noninvasive sensor signal indicative of the received light. The sensor signal is proportional to the volume of blood in the artery.

In this aspect, the pressure perturbation is dependent on the patient's arterial compliance. Since the vibrating element 352 provides a constant pressure to the chamber 354, the resulting noninvasive sensor signal amplitude (by detector 360) is proportional to the compliance of the patient's artery. If the artery is highly compliant (flexible), the noninvasive sensor signal will have a relatively small amplitude as the pulse propagates through the artery. If the artery is not compliant (stiff), the noninvasive sensor signal will have a relatively large amplitude as the pulse propagates through the artery. As a result, the noninvasive sensor signal amplitude provides information that is directly dependent on the patient's arterial compliance. This information is very useful to physicians. Since compliance varies as pressure varies during the pulse, the noninvasive sensor signal amplitude varies as the pressure varies during the cardiac cycle. Thus, this embodiment also provides a convenient, motion insensitive, method for determining the pulse.

A notable feature is described regarding the constant pressure feedback signal from sensor 356. Since the object of the constant pressure embodiment is to maintain constant pressure in chamber 354, the feedback signal from sensor 356 is important to gauge the displacement by exciter 352 to maintain the constant pressure. As a result, the feedback signal also provides information that is directly dependent on the patient's arterial compliance. As in the above embodiments the signal can also be used to determine the patient's pulse.

OSCILLOMETRY APPLICATION

The invention can also be used in an oscillometric apparatus to determine the patient's blood pressure. The invention is positioned under an occlusive cuff. When the cuff is inflated, the sensor signal will increase in amplitude due to the increased pressure and the response by the artery to the pressure. When the cuff pressure reaches the diastolic pressure, the sensor signal will begin to increase in amplitude in a rapid manner because the cuff pressure exceeds the diastolic pressure in the artery. When the cuff pressure reaches the mean arterial pressure, the sensor signal is maximized. Above the means arterial pressure, the sensor signal will begin to decrease in amplitude in a rapid manner because the cuff pressure is approaching the systolic pressure and the blood flow is decreasing through the artery. Once the cuff pressure exceeds the systolic pressure the sensor signal is attenuated because the cuff prevents blood flow in the artery. The invention can accurately track the pulse amplitude and can identify the diastolic, mean and systolic pressures correlated to the occlusive cuff. The invention has improved characteristics over known oscillometric techniques because the invention can identify the pulse in the presence of motion which can occur often while using an oscillometric cuff.

FREQUENCY DOMAIN PROCESSING ALTERNATIVE

While the processing system described in the embodiments involves the use of a time domain lock-in amplifier 143, it will be clear to those persons skilled in the art that similar results can be achieved by frequency domain processing. For example, a Fourier transform can be performed on the various signals to be analyzed, and processing in the frequency domain can be further performed that is analogous to the described processing by the lock-in amplifier in the time domain. The various filtering steps described above can be advantageously performed in the frequency domain. Processing steps in the frequency domain are considered as falling within the general category of the analysis of the transfer function between the exciter sensor waveform and the noninvasive sensor waveform and are intended to be covered by the claims. The variety of techniques that are used in the art for the calculation of transfer functions are also applicable to this analysis.

VARIATIONS ON THE DISCLOSED EMBODIMENTS

Additional embodiments include an embodiment in which two or more sensors are positioned along the artery at different distances from a single exciter, and an embodiment in which two or more exciters are positioned along the artery at different distances from one or more sensors. In each of these embodiments, the information obtained from each exciter sensor pair can be analyzed independently. The multiply redundant measurements of pulse that result can be combined to provide a single pulse determination that may be both more accurate and more immune from motion artifact, noise, and other interference sources. Moreover, the information obtained from each sensor can be compared and the time delay between the sensors calculated. This would provide time difference of arrival information that could be used to determine a pulse. Similar redundancy can be achieved in the embodiments that use multiple exciter waveforms by analyzing the results at each frequency independently and combining the results to provide enhanced robustness.

CONCLUSION

A close relationship between physiological parameters and hemoparameters supplies valuable information used in the present invention. The perturbation of body tissue and sensing the perturbation also supplies valuable information used in the present invention. This technology could be used in a variety of applications where noninvasive measurement of the cardiac pulse is required. The simplest example is a device that measures heart rate in a motion insensitive way. Other examples include: detecting the return of blood flow in an occlusive cuff blood pressure measurement device, detecting the pulse for a pulse oximeter, or detecting a pulse for the determination of blood pressure by the oscillometric technique.

The exciter of the preferred embodiment uses air, but any suitable fluid can be used. Moreover, various exciter techniques can be used for inducing an exciter waveform into the patient such as an acoustic exciter, an electromagnetic exciter and an electromechanical exciter (e.g. piezoelectric device).

Various noninvasive sensors have been developed for sensing hemoparameters. These sensor types include piezoelectric, piezoresistive, impedance plethysmograph, photoplethysmograph, various types of strain gages, air cuffs, tonometry, conductivity, resistivity and other devices. The present invention can use any sensor that provides a waveform related to the hemoparameter of interest.

Having disclosed exemplary embodiments and the best mode, modifications and variations may be made to the disclosed embodiments while remaining within the subject and spirit of the invention as defined by the following claims.

What is claimed is:

1. A motion insensitive pulse detector for determining a patient's pulse, comprising:

an exciter adapted to be positioned over a blood vessel of the patient and configured to induce a transmitted exciter waveform into the patient;

a noninvasive sensor adapted to be positioned over said blood vessel and configured to sense a hemoparameter and to generate a noninvasive sensor signal representative of said hemoparameter containing a plurality of components including a received exciter waveform component, a physiological waveform component, and a motion component; and a processor coupled to said noninvasive sensor and configured to receive said noninvasive sensor signal, said processor having a filter configured to separate said received exciter waveform component from said physiological waveform component and said motion component and wherein said processor is configured to determine the patient's pulse based at least in part on said received exciter waveform component.

2. The motion insensitive pulse detector of claim 1, wherein:

said received exciter waveform component has a frequency bandwidth substantially outside the frequency bandwidth of the motion component;

said filter is configured to separate from said noninvasive sensor signal said received exciter waveform having a frequency bandwidth outside of the frequency bandwidth of the motion component; and said processor is configured to determine the patient's pulse based at least in part on said received exciter waveform.

3. The motion insensitive pulse detector of claim 1, wherein:

said received exciter waveform component has a time-varying component;

said filter is configured to separate from said noninvasive sensor signal said received exciter waveform having a time-varying component; and said processor is configured to determine the patient's pulse based at least in part on said time-varying component.

4. The motion insensitive pulse detector of claim 1, wherein:

said received exciter waveform component has a time-varying phase;

said filter is configured to separate from said noninvasive sensor signal said received exciter waveform having a time-varying phase; and said processor is configured to determine the patient's pulse based at least in part on said time-varying phase.

5. The motion insensitive pulse detector of claim 1, wherein:

said processor is configured to determine the patient's pulse based at least in part on a correlation between said received exciter waveform and said transmitted exciter waveform.

6. The motion insensitive pulse detector of claim 1, wherein:

said noninvasive sensor is configured to be positioned at a distance from said exciter.

7. The motion insensitive pulse detector of claim 6, further comprising:

an oscillometric cuff configured to be placed over said exciter and over said noninvasive sensor and configured to inflate to a predetermined pressure; and wherein said processor is configured to determine the patient's pulse as said oscillometric cuff inflates.

8. The motion insensitive pulse detector of claim 1, further comprising:

an oscillometric cuff configured to be placed over said exciter and over said noninvasive sensor and configured to inflate to a predetermined pressure; and wherein said processor is configured to determine the patient's pulse as said oscillometric cuff inflates.

9. The motion insensitive pulse detector of one of claims 1, 2, 3, 4 or 5, wherein:

said filter is configured to separate from said received exciter waveform a signal exciter waveform and a noise waveform; and said processor is configured to determine the patient's pulse based at least in part on said signal exciter waveform.

10. The motion insensitive pulse detector of one of claims 1, 2, 3, 4 or 5, wherein:

said filter is configured to determine an arc representing time-varying positions of said received exciter waveform, to determine a center point of said arc and to determine a motion vector from an origin to said center point;

said filter is configured to determine an arc vector from said center point to said time-varying positions, where said arc vector has an arc vector angle that moves from a first angle to a second angle over time; and said processor is configured to determine the patient's pulse based at least in part on said arc vector angle.

11. The motion insensitive pulse detector of one of claims 1, 2, 3, 4 or 5, wherein:

said filter is configured to determine an arc representing time-varying positions of said received exciter waveform, to determine a center point of said arc and to determine a motion vector from an origin to said center point;

said filter is configured to determine an arc vector from said center point to said time-varying positions, where said arc vector has an arc vector angle that moves from a first angle to a second angle over time;

said filter is configured to determine from said arc vector a signal exciter vector and a noise vector; and said processor is configured to determine the patient's pulse based at least in part on said signal exciter vector.

12. The motion insensitive pulse detector of claim 1, wherein:

said exciter is adapted to have a substantially constant coupling between the patient and said exciter; and said noninvasive sensor is adapted to have a substantially constant coupling between the patient and said noninvasive sensor.

13. The motion insensitive pulse detector of claim 12, wherein:

said exciter has a relatively low mass; and said noninvasive sensor has a relatively low mass.

14. A processor for determining a patient's pulse with an apparatus having an exciter adapted to be positioned over a blood vessel of the patient and configured to induce a transmitted exciter waveform into the patients and a noninvasive sensor adapted to be positioned over said blood vessel and configured to sense a hemoparameter and to generate a noninvasive sensor signal representative of said hemoparameter containing a plurality of components including a received exciter waveform component, a physiological waveform component, and a motion component, said processor comprising:

an input configured to receive said noninvasive sensor signal;

a filter configured to separate said received exciter waveform component from said physiological waveform component and said motion component; and a determination routine configured to process said noninvasive sensor signal to determine the patient's pulse based at least in part on said received exciter waveform component.

15. The processor of claim 14, wherein:

said received exciter waveform component has a frequency bandwidth substantially outside the frequency bandwidth of the motion component; and said filter is configured to separate from said noninvasive sensor signal said motion component and said received exciter waveform having a frequency bandwidth outside the frequency bandwidth of the motion component.

16. The processor of claim 14, wherein:

said received exciter waveform component has a time-varying component;

said filter is configured to separate from said noninvasive sensor signal said received exciter waveform having a time-varying component; and said determination routine is configured to determine the patient's pulse based at least in part on said time-varying component.

17. The processor of claim 14, wherein:

said received exciter waveform component has a time-varying phase;

said filter is configured to separate from said noninvasive sensor signal said received exciter waveform having a time-varying phase; and said determination routine is configured to determine the patient's pulse based at least in part on said time-varying phase.

18. The processor of claim 14, wherein:

said determination routine is configured to determine the patient's pulse based at least in part on a correlation between said received exciter waveform and said transmitted exciter waveform.

19. The processor of one of claims 14, 15, 16, 17 or 18, wherein:

said filter is configured to separate from said received exciter waveform a signal exciter waveform and a noise waveform; and said determination routine is configured to determine the patient's pulse based at least in part on said signal exciter waveform.

20. The processor of one of claims 14, 15, 16, 17 or 18, wherein:

said filter is configured to determine an arc representing time-varying positions of said received exciter waveform, to determine a center point of said arc and to determine a motion vector from an origin to said center point;

said filter is configured to determine an arc vector from said center point to said time-varying positions, where said arc vector has an arc vector angle that moves from a first angle to a second angle over time; and said determination routine is configured to determine the patient's pulse based at least in part on said arc vector angle.

21. The processor of one of claims 14, 15, 16, 17 or 18, wherein:

said filter is configured to determine an arc representing time-varying positions of said received exciter waveform, to determine a center point of said arc and to determine a motion vector from an origin to said center point;

said filter is configured to determine an arc vector from said center point to said time-varying positions, where said arc vector has an arc vector angle that moves from a first angle to a second angle over time;

said filter is configured to determine from said arc vector a signal exciter vector and a noise vector; and said determination routine is configured to determine the patient's pulse based at least in part on said signal exciter vector.

22. A method of determining a patient's pulse, comprising the steps of:

inducing a transmitted exciter waveform into the patient;

noninvasively sensing a hemoparameter and generating a noninvasive sensor signal representative of said hemoparameter containing a plurality of components including a received exciter waveform component, a physiological waveform component, and a motion component; and processing said noninvasive sensor by performing the steps including:

separating said received exciter waveform component from said physiological waveform component and said motion component; and determining the patient's pulse based at least in part on said received exciter waveform component.

23. The method of claim 22, wherein:

said received exciter waveform component has a frequency bandwidth substantially outside the frequency bandwidth of the motion component;

said processing step includes a step of separating from said noninvasive sensor signal said received exciter waveform having a frequency bandwidth outside of the frequency bandwidth of the motion component; and said processing step includes a step of determining the patient's pulse based at least in part on said received exciter waveform.

24. The method of claim 22, wherein:

said received exciter waveform component has a time-varying component;

said processing step includes a step of separating from said noninvasive sensor signal said received exciter waveform having a time-varying component; and said processing step includes a step of determining the patient's pulse based at least in part on said time-varying component.

25. The method of claim 22, wherein:

said received exciter waveform component has a time-varying phase;

said processing step includes a step of separating from said noninvasive sensor signal said received exciter waveform having a time-varying phase; and said processing step includes a step of determining the patient's pulse based at least in part on said time-varying phase.

26. The method of claim 22, wherein:

said processing step includes a step of determining the patient's pulse based at least in part on a correlation between said received exciter waveform and said transmitted exciter waveform.

27. The method of claim 22, further comprising the step of:

inflating an oscillometric cuff over a portion of the patient where said inducing step is performed and where said noninvasively sensing step is performed; and wherein said processing step is performed by processing said noninvasive sensor signal to determine the patient's pulse during said inflating step.

28. The method of one of claims 22, 23, 24, 25 or 26, wherein:

said processing step includes a step of separating from said received exciter waveform a signal exciter waveform and a noise waveform; and said processing step includes a step of determining the patient's pulse based at least in part on said signal exciter waveform.

29. The method of one of claims 22, 23, 24, 25 or 26, wherein:

said processing step includes a step of determining an arc representing time-varying positions of said received exciter waveform, to determine a center point of said arc and to determine a motion vector from an origin to said center point;

said processing step includes a step of determining an arc vector from said center point to said time-varying positions, where said arc vector has an arc vector angle that moves from a first angle to a second angle over time; and said processing step includes a step of determining the patient's pulse based at least in part on said arc vector angle.

30. The method of one of claims 22, 23, 24, 25 or 26, wherein:

said processing step includes a step of determining an arc representing time-varying positions of said received exciter waveform, to determine a center point of said arc and to determine a motion vector from an origin to said center point;

said processing step includes a step of determining an arc vector from said center point to said time-varying positions, where said arc vector has an arc vector angle that moves from a first angle to a second angle over time;

said processing step includes a step of determining from said arc vector a signal exciter vector and a noise vector; and said processing step includes a step of determining the patient's pulse based at least in part on said signal exciter vector.

* * * * *